(12) United States Patent
Blackwell et al.

(10) Patent No.: US 9,385,033 B2
(45) Date of Patent: Jul. 5, 2016

(54) METHOD OF FORMING A METAL FROM A COBALT METAL PRECURSOR

(71) Applicants: James M. Blackwell, Portland, OR (US); Scott B. Clendenning, Portland, OR (US); John J. Plombon, Portland, OR (US); Patricio E. Romero, Portland, OR (US)

(72) Inventors: James M. Blackwell, Portland, OR (US); Scott B. Clendenning, Portland, OR (US); John J. Plombon, Portland, OR (US); Patricio E. Romero, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 86 days.

(21) Appl. No.: 14/040,109

(22) Filed: Sep. 27, 2013

(65) Prior Publication Data
US 2015/0093890 A1   Apr. 2, 2015

(51) Int. Cl.
| | |
|---|---|
| H01L 21/06 | (2006.01) |
| H01L 21/768 | (2006.01) |
| C07F 15/06 | (2006.01) |
| C23C 16/06 | (2006.01) |
| C23C 16/16 | (2006.01) |
| C23C 16/18 | (2006.01) |
| C23C 16/455 | (2006.01) |
| H01L 21/285 | (2006.01) |

(52) U.S. Cl.
CPC .......... *H01L 21/76843* (2013.01); *C07F 15/06* (2013.01); *C23C 16/06* (2013.01); *C23C 16/16* (2013.01); *C23C 16/18* (2013.01); *C23C 16/45553* (2013.01); *H01L 21/28556* (2013.01); *H01L 21/28562* (2013.01); *H01L 21/76898* (2013.01)

(58) Field of Classification Search
CPC .............................. H01L 21/285; H01L 29/45
USPC ....................... 438/602; 556/7, 11, 12, 16, 31
See application file for complete search history.

(56) References Cited

U.S. PATENT DOCUMENTS

| | | | | |
|---|---|---|---|---|
| 6,849,122 | B1 * | 2/2005 | Fair .......................... | C23C 16/18 117/102 |
| 7,014,709 | B1 * | 3/2006 | Fair .......................... | C23C 16/16 117/89 |
| 7,285,493 | B2 * | 10/2007 | Kang ...................... | C23C 16/16 257/E21.17 |
| 8,372,473 | B2 * | 2/2013 | Dussarrat ................ | C07F 17/00 427/126.6 |
| 2007/0269956 | A1 * | 11/2007 | Lavoie ................ | H01L 21/7682 438/421 |
| 2008/0064205 | A1 * | 3/2008 | Dominguez ............ | C23C 16/34 438/653 |

(Continued)

FOREIGN PATENT DOCUMENTS

WO   WO-2012150133   11/2012

*Primary Examiner* — Caleb Henry
(74) *Attorney, Agent, or Firm* — Blakely, Sokoloff, Taylor & Zafman LLP

(57) ABSTRACT

A metal precursor and a method comprising decomposing a metal precursor on an integrated circuit device; and forming a metal from the metal precursor, wherein the metal precursor is selected from the group consisting of (i) a $Co_2(CO)_6$ ($R^1C\equiv CR^2$), wherein $R^1$ and $R^2$ are individually selected from a straight or branched monovalent hydrocarbon group have one to six carbon atoms that may be interrupted and substituted; (ii) a mononuclear cobalt carbonyl nitrosyl; (iii) a cobalt carbonyl bonded to one of a boron, indium, germanium and tin moiety; (iv) a cobalt carbonyl bonded to a mononuclear or binuclear allyl; and (v) a cobalt(II) complex comprising nitrogen-based supporting ligands.

10 Claims, 2 Drawing Sheets

(56) References Cited

U.S. PATENT DOCUMENTS

| | | | |
|---|---|---|---|
| 2009/0018330 A1* | 1/2009 | Molt et al. | 544/64 |
| 2009/0175775 A1* | 7/2009 | Alberto et al. | 423/413 |
| 2011/0086509 A1* | 4/2011 | Ganguli et al. | 438/655 |
| 2012/0215000 A1* | 8/2012 | Tsai | 546/4 |
| 2012/0252207 A1 | 10/2012 | Lei et al. | |
| 2013/0072015 A1* | 3/2013 | Chen et al. | 438/663 |
| 2013/0270513 A1* | 10/2013 | Romero et al. | 257/9 |
| 2014/0158937 A1* | 6/2014 | Jang | C09K 11/025 252/301.36 |
| 2014/0179105 A1* | 6/2014 | Lansalot-matras et al. | 438/681 |
| 2014/0349480 A1* | 11/2014 | Shek et al. | 438/652 |
| 2015/0038660 A1* | 2/2015 | Taftaf et al. | 526/210 |
| 2015/0093891 A1* | 4/2015 | Zope | H01L 21/768 438/618 |
| 2015/0104371 A1* | 4/2015 | Peters et al. | 423/352 |
| 2015/0246941 A1* | 9/2015 | Peters | C23C 16/18 427/252 |

\* cited by examiner

METHOD OF FORMING A METAL FROM A COBALT METAL PRECURSOR

FIELD

Metallization in integrated circuit devices.

BACKGROUND

Generally, limited atomic layer deposition (ALD)/chemical vapor deposition (CVD) precursor options currently exist for delivering high purity cobalt films. These options tend to be even more limited when requirements such as source stability, high deposition rate for thermal only ALD/CVD and liquid physical state at source temperature are considered. One commercially available precursor, µ2-η2-tertbutylacetylenedicobalthexacarbonyl (CCTBA) suffers from low thermal stability. Low thermal stability leads to decomposition to an intractable solid in a source ampoule under delivery conditions which negatively impacts precursor dose as well as a functionality of a source liquid level sensor both of which are undesirable.

DETAILED DESCRIPTION

Figure 1:
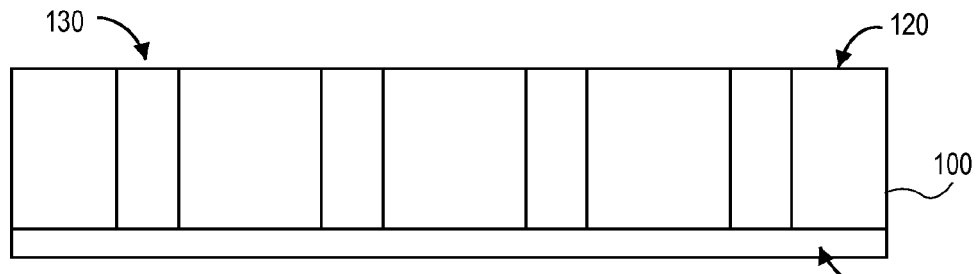
FIG. 1 is a cross-section of a portion of a semiconductor substrate including a device side and formed from the device side to an opposite side of the substrate.

Methods for introducing transition metals on integrated circuit substrate used are described. In one embodiment, methods for introducing a cobalt metal by way of a cobalt precursor are described.

In one embodiment, a method includes decomposing a transition metal precursor (e.g., a cobalt metal precursor) on an integrated circuit device and forming a metal from the metal precursor. In one embodiment, the metal precursor is selected from:

(i) a $Co_2(CO)_6(R^1C\equiv C^2)$, wherein $R^1$ and $R^2$ are each individually selected from a straight or branched monovalent hydrocarbon group have one to six carbon atoms that may be interrupted and substituted;

(ii) a mononuclear cobalt carbonyl nitrosyl;

(iii) a cobalt carbonyl bonded to one of a boron, indium, germanium and tin moiety;

(iv) a cobalt carbonyl bonded to a mononuclear or binuclear allyl; and (v) a cobalt(II) complex comprising nitrogen-based supporting ligands.

In an embodiment where the metal precursor is $Co_2(CO)_6$ ($R^1C\equiv CR^2$), an internal alkyne, tert-butylacetylene bridging a dicobalt-hexacarbonyl core is described. An internal alkyne is defined as an alkyne with $R^1$ and $R^2$ substituents defining the acetylene ($R^1C\equiv CR^2$) as opposed to a terminal alkyne which includes one substituent and a hydrogen (e.g., $R^1C\equiv CH$). CCTBA is an example of a terminal alkyne, tert-butylacetylene bridging a dicobalt-hexacarbonyl core.

In an embodiment where the metal precursor is $Co_2(CO)_6$ ($R^1C\equiv CR^2$), $R^1$ and $R^2$ are individually selected from a straight or branched hydrocarbon group having one to six carbon atoms which may be interrupted and/or substituted. Monovalent hydrocarbons, in one embodiment, include a straight or branched chain alkyl. Such straight or branched chain alkyl has one to six carbon atoms, in one embodiment, and one to four carbon atoms in another embodiment. An interruption is an interruption in a chain of carbon atoms. In one embodiment, a straight or branched chain carbon atoms may be interrupted by oxygen atom, a sulfur atom or a nitrogen atom. In addition to embodiments allowing for interruptions of a hydrocarbon group, in another embodiment, substituents of the hydrocarbon group (e.g., carbon atoms) may be substituted with, for example, halide groups (e.g., $CF_3$). A representative hydrocarbon group that is both interrupted and substituted is, for example, an ester. In one embodiment, the monovalent hydrocarbon group may be saturated (e.g., an alkyl) or unsaturated (e.g., the group may contain one or more double bonds).

Examples of representative precursors having the general formula $Co_2(CO)_6(R^1C\equiv CR^2)$ where $R^1$ and $R^2$ each individually selected from alkyl groups having four or less carbon atoms are the following:

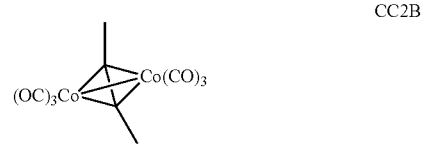

CC2B

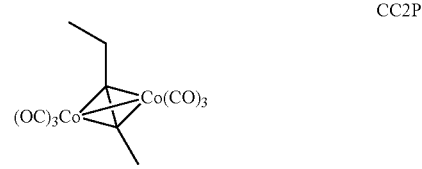

CC2P

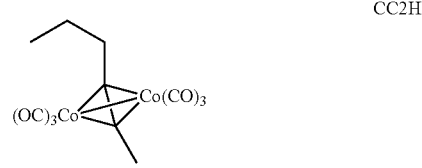

CC2H

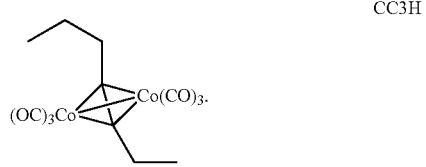

CC3H

In another embodiment, a suitable cobalt precursor for forming a metal from the precursor on an integrated circuit substrate is a mononuclear cobalt carbonyl nitrosyl. Examples of mononuclear cobalt carbonyl nitrosyl include, but are not limited to:

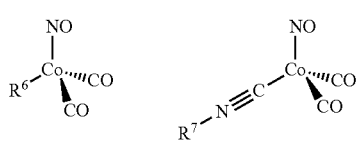

-continued

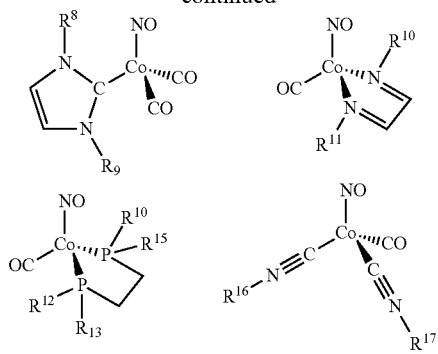

wherein $R^7$, $R^8$, $R^9$, $R^{10}$, $R^{11}$, $R^{12}$, $R^{13}$, $R^{14}$, $R^{15}$, $R^{16}$ and $R^{17}$ are independently selected from a straight or branched chain alkyl having one to four carbon atoms.

In another embodiment, suitable cobalt precursors for forming a metal from the precursor on integrated circuit substrate include a cobalt carbonyl bonded to one of a boron, indium, germanium and tin moiety. Representative cobalt precursors include, but are not limited to:

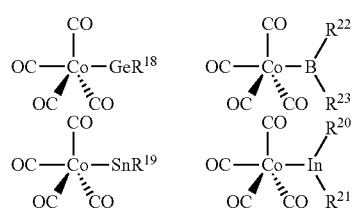

wherein $R^{18}$, $R^{19}$, $R^{20}$, $R^{21}$, $R^{22}$ and $R^{23}$ are independently selected from a straight or branched chain alkyl having one to four carbon atoms and $R^{20}$ and $R^{21}$ may further individually be a substituted amine.

In another embodiment, a suitable cobalt precursor for forming a metal from the precursor on an integrated circuit substrate is a cobalt carbonyl bonded to a mononuclear or binuclear allyl. Representative examples include, but are not limited to:

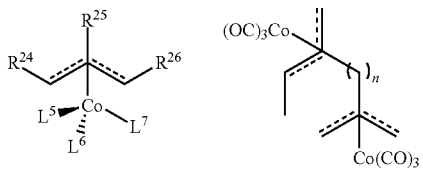

wherein $R^{24}$, $R^{25}$ and $R^{26}$ are independently selected from a straight or branched chain alkyl having one to the three carbon atoms and $L^5$, $L^6$ and $L^7$ are independently selected from one of:

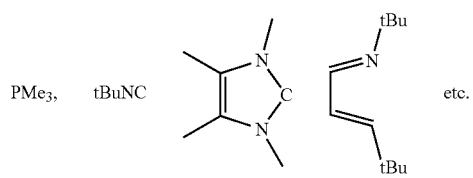

In a further embodiment, suitable metal precursors for forming a metal precursor on an integrated circuit include a cobalt (II) complex comprising nitrogen-based supporting ligands. Representative examples include:

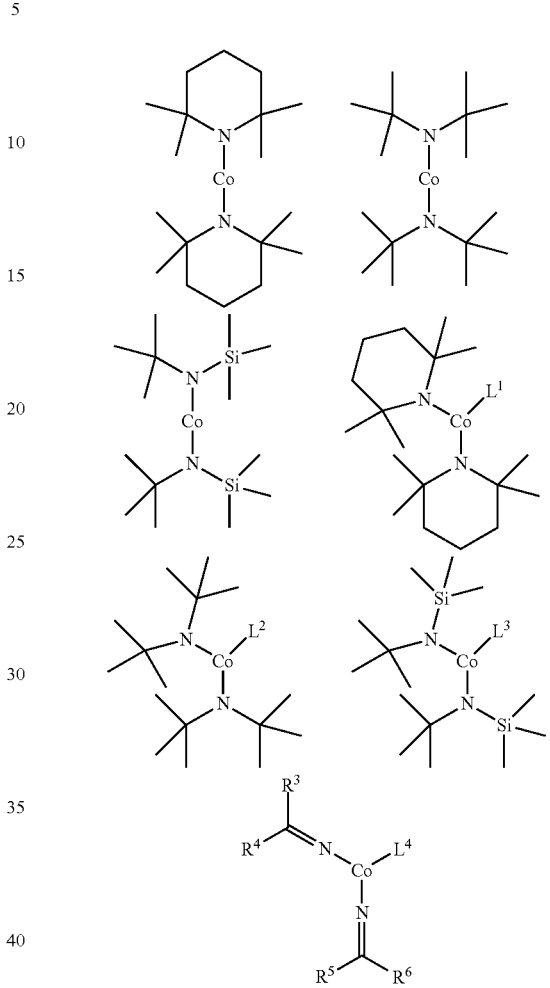

wherein $R^3$, $R^4$, $R^5$ and $R^6$ are individually selected from a straight or branched monovalent hydrocarbon group have one to three carbon atoms that may be substituted and $L^1$, $L^2$, $L^3$ and $L^4$ are independently selected from a substituted amine and quinuclidine.

A transition metal precursor such as a cobalt metal precursor described above may be used to form a metal, such as a cobalt metal on an integrated circuit. One embodiment for forming a cobalt metal from one of the noted precursor utilizes a coreactant introduced simultaneously with or subsequent to the introduction of the precursor to decompose the precursor to cobalt metal. Suitable coreactants include, but are not limited to, a hydrogen gas or hydrogen plasma; an ammonia gas or ammonia plasma; a hydrozine such as $N_2H_4$, methylhydrazine or tertiarybutylhydrazine; a borane such as diborane or an organoborane; an alane; or a silane such as monosilane, disilane or higher order silane. In one embodiment, a semiconductor substrate (e.g., integrated circuit substrate) is placed in a chamber suitable for CVD or ALD processing and the precursor and a coreactant are introduced.

Cobalt is a metal that has been utilized in multilevel metallization processes especially for PMOS work function layers of metal oxide semiconductor field effect transistors (MOSFETs). Cobalt metal has also been used as a barrier material for an interconnect line such as a barrier for a copper interconnect (to inhibit migration of copper into an adjacent dielectric material). Cobalt metal can also be used as interconnect material.

One application of the use of cobalt in the course of an integrated circuit process is a process for metallization of through-silicon vias (TSVs). TSVs are utilized to produce three-dimensional integrated circuit chip arrangements and allow for die-to-die stacking such as, for example, stacking of dynamic random access memory (DRAM) on a microprocessor die (e.g., wide I/O memory configuration).

FIGS. 1-4 illustrate a process for forming TSVs. FIG. 1 shows a cross-sectional side view of a portion of an integrated circuit substrate, such as a portion of a silicon chip at, for example, the wafer stage. Substrate 100 of portion of a chip includes device side 110 representatively having a number of devices formed therein and thereon and back side 120 opposite device side 110. Disposed within substrate 100 or through substrate 100 are TSVs 130 which extend from device side 110 to back side 120. TSVs 130 may be formed by an etching process.

Figure 2:
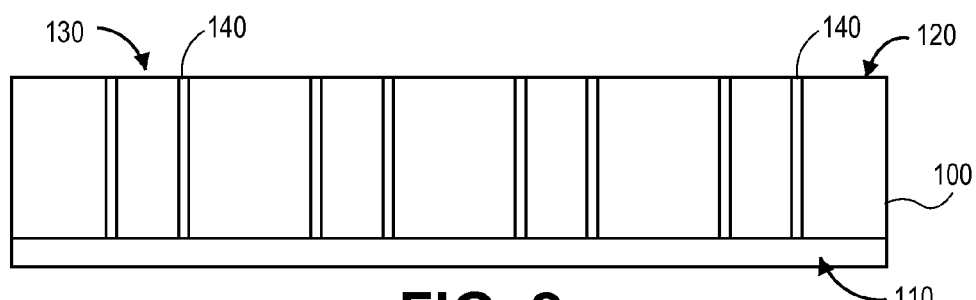
FIG. 2 shows the structure of FIG. 1 following the introduction of a dielectric layer on the sidewalls of the vias.

FIG. 2 shows the structure of FIG. 1 following the introduction of a dielectric material into vias 130. FIG. 2 shows dielectric material 140 of, for example, a silicon dioxide or insulating polymer introduced (deposited) along the sidewalls of vias 130.

Figure 3:
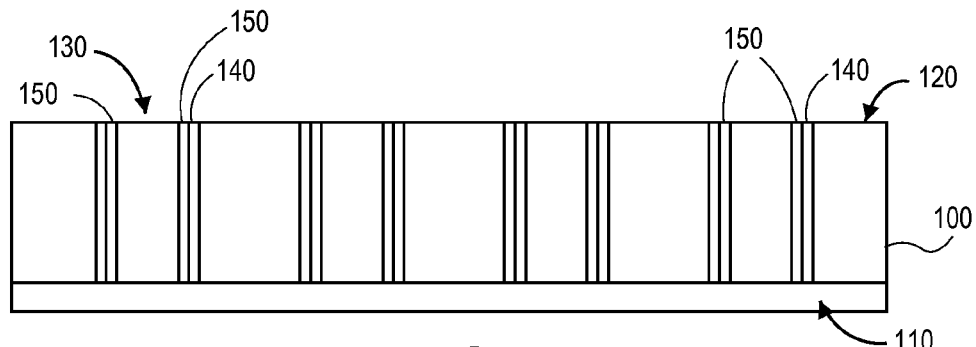
FIG. 3 shows the structure of FIG. 2 following the introduction of a barrier layer or the dielectric layer.

FIG. 3 shows the structure of FIG. 2 following the introduction of a barrier layer in the vias. Referring to FIG. 3, FIG. 3 shows barrier layer 150 disposed along the sidewalls of via 130 on dielectric layer 140. In one embodiment, barrier layer 150 is a transition metal, particularly cobalt. A transition metal of cobalt may be deposited by ALD or CVD techniques utilizing a cobalt metal precursor such as described above. In a chamber suitable for ALD or CVD process, a metal precursor is introduced into via 130 and decomposes in via to a cobalt metal. One way to confine the introduction of cobalt metal into the vias is by masking back side 120 of the substrate. One way to foster the decomposition of the cobalt metal precursor is through the introduction of a hydrogen gas, representatively introduced with the precursor. FIG. 3 shows the structure following the decomposition of the precursor and the formation of barrier layer (cobalt metal layer) 150 in vias 130.

Figure 4:
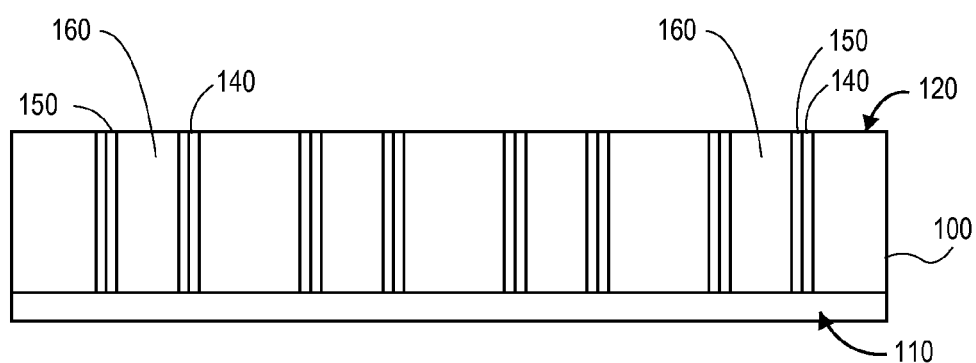
FIG. 4 shows the structure of FIG. 3 following the introduction of a conductive material in the vias and the formation of through-silicon vias (TSVs).

FIG. 4 shows the structure of FIG. 3 following the introduction of a conductive material such as copper in the vias. FIG. 4 shows conductive material 160 of, for example, electrodeposited copper disposed in and filling the vias.

It is appreciated that the above example is one example of depositing and use for a cobalt metal. The precursors described herein may be used in such a process for such use or any other process or use involving circuits or semiconductor substrates.

Figure 5:
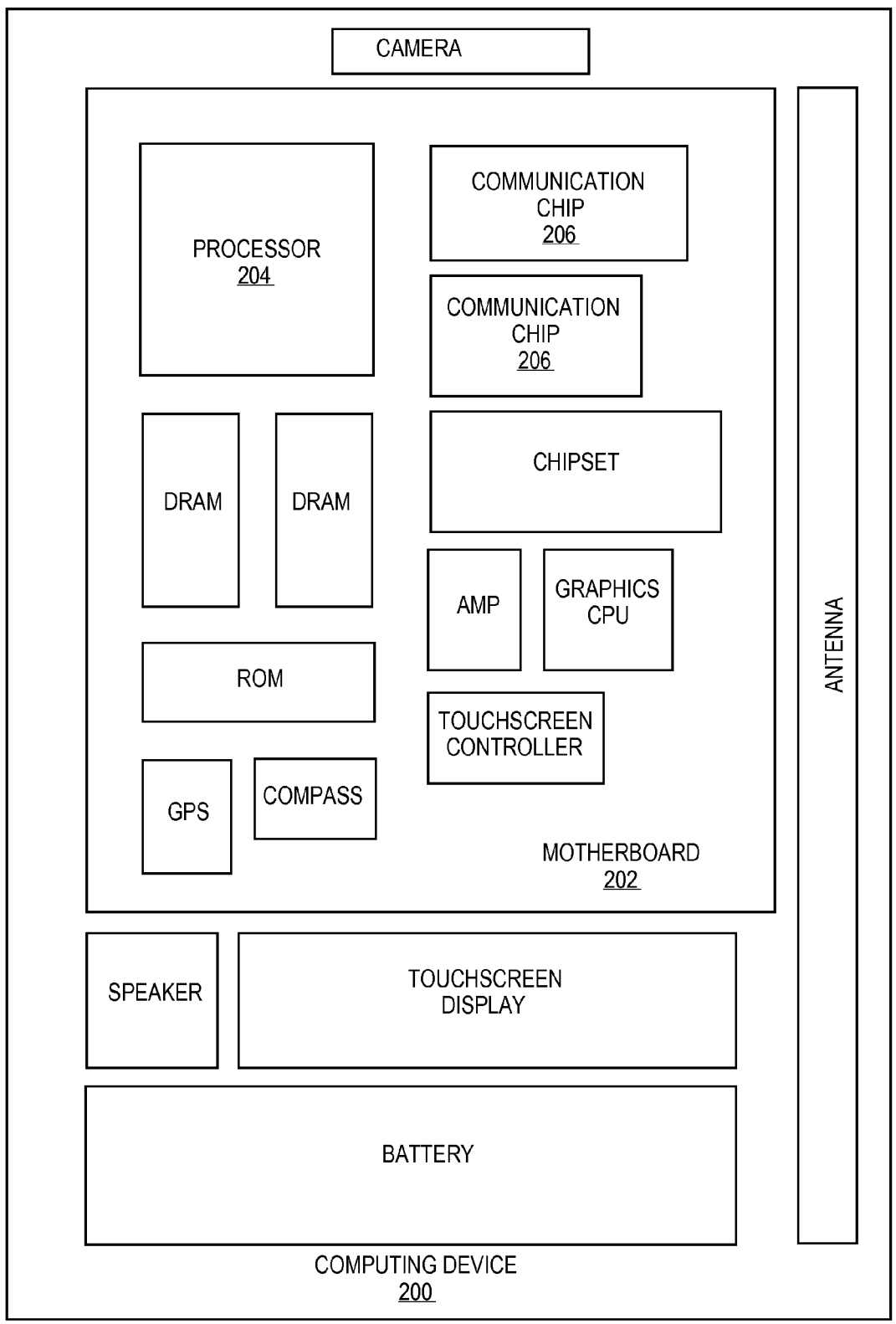
FIG. 5 illustrates computing device in accordance with one implementation of the invention.

FIG. 5 illustrates a computing device 200 in accordance with one implementation. Computing device 200 houses board 202. Board 202 may include a number of components, including but not limited to processor 204 and at least one communication chip 206. Processor 204 is physically and electrically connected to board 202. In some implementations at least one communication chip 206 is also physically and electrically connected to board 202. In further implementations, communication chip 206 is part of processor 204.

Depending on its applications, computing device 200 may include other components that may or may not be physically and electrically connected to board 202. These other components include, but are not limited to, volatile memory (e.g., DRAM), non-volatile memory (e.g., ROM), flash memory, a graphics processor, a digital signal processor, a crypto processor, a chipset, an antenna, a display, a touchscreen display, a touchscreen controller, a battery, an audio codec, a video codec, a power amplifier, a global positioning system (GPS) device, a compass, an accelerometer, a gyroscope, a speaker, a camera, and a mass storage device (such as hard disk drive, compact disk (CD), digital versatile disk (DVD), and so forth). Representatively, processor 204 is a system on chip and is packaged in a microprocessor package assembly such as described above with a DRAM die connected to a backside of processor 204 in a wide I/O configuration and another memory device (e.g., a DRAM device) also connected to the package.

Communication chip 206 enables wireless communications for the transfer of data to and from computing device 200. The term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. Communication chip 206 may implement any of a number of wireless standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, derivatives thereof, as well as any other wireless protocols that are designated as 3G, 4G, 5G, and beyond. Computing device 200 may include a plurality of communication chips 206. For instance, a first communication chip 206 may be dedicated to shorter range wireless communications such as Wi-Fi and Bluetooth and a second communication chip 206 may be dedicated to longer range wireless communications such as GPS, EDGE, GPRS, CDMA, WiMAX, LTE, Ev-DO, and others.

Communication chip 206 also includes an integrated circuit die packaged within communication chip 206 such as described above. The die may include a cobalt metal introduced by way of one of the above-noted precursors and used, for example, as a silicide for a transistor, an interconnect or a barrier layer for an interconnect or TSV.

In further implementations, another component housed within computing device 200 may contain a microelectronic package including an integrated circuit die such as described above.

In various implementations, computing device 200 may be a laptop, a netbook, a notebook, an ultrabook, a smartphone, a tablet, a personal digital assistant (PDA), an ultra mobile PC, a mobile phone, a desktop computer, a server, a printer, a scanner, a monitor, a set-top box, an entertainment control unit, a digital camera, a portable music player, or a digital video recorder. In further implementations, computing device 200 may be any other electronic device that processes data.

In the description above, for the purposes of explanation, numerous specific details have been set forth in order to provide a thorough understanding of the embodiments. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
   decomposing a metal precursor on an integrated circuit device; and
   forming a metal from the metal precursor,
   wherein the metal precursor is selected from the group consisting of:
   (i) a mononuclear cobalt monocarbonyl nitrosyl or cobalt dicarbonyl nitrosyl;
   (ii) a cobalt carbonyl bonded to one of a boron, indium, germanium and tin moiety;
   (iii) a mononuclear cobalt carbonyl bonded to a mononuclear or binuclear allyl; and
   (iv) a cobalt(II) complex comprising nitrogen-based supporting ligands selected from the group consisting of:

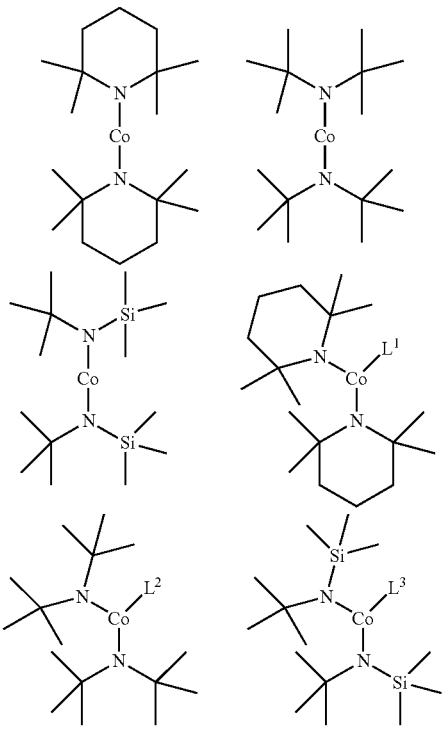

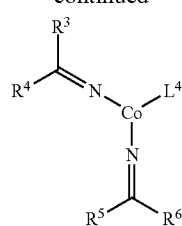

wherein $R^3$, $R^4$, $R^5$ and $R^6$ are individually selected from a straight or branched monovalent hydrocarbon group have one to three carbon atoms that may be substituted and $L^1$, $L^2$, $L^3$ and $L^4$ are independently selected from a substituted amine and quinuclidine.

2. The method of claim 1, wherein the metal precursor comprises a mononuclear cobalt carbonyl nitrosyl selected from the group consisting of:

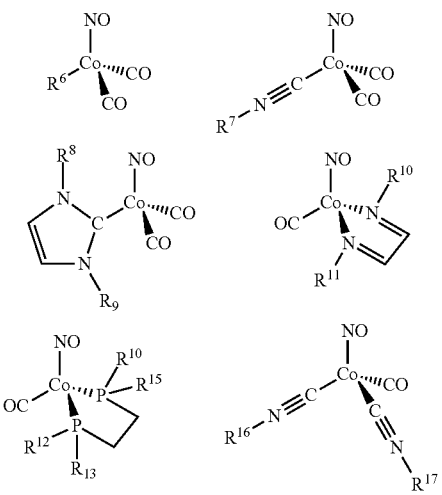

wherein $R^7$, $R^8$, $R^9$, $R^{10}$, $R^{11}$, $R^{12}$, $R^{13}$, $R^{14}$, $R^{15}$, $R^{16}$ and $R^{17}$ are independently selected from a straight or branched chain alkyl having one to four carbon atoms.

3. The method of claim 1, wherein the metal precursor is selected from the group consisting of:

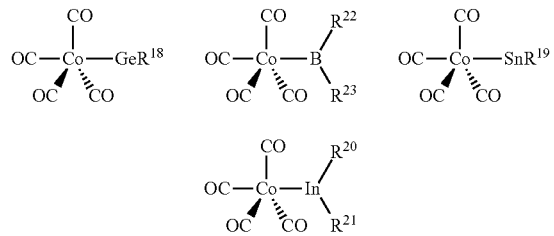

wherein $R^{18}$, $R^{19}$, $R^{20}$, $R^{21}$, $R^{22}$ and $R^{23}$ are independently selected from a straight or branched chain alkyl having one to four carbon atoms and $R^{20}$ and $R^{21}$ may further individually be a substituted amine.

4. The method of claim 1, wherein the metal precursor is selected from the group consisting of:

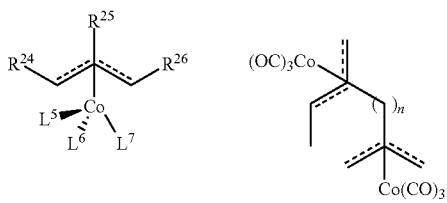

wherein $R^{24}$, $R^{25}$ and $R^{26}$ are independently selected from a straight or branched chain alkyl having one to the three carbon atoms and $L^5$, $L^6$ and $L^7$ are independently selected from the group consisting of:

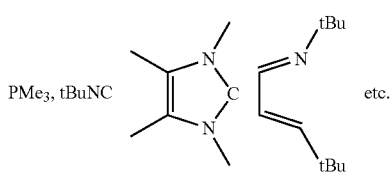

5. The method of claim 1, wherein forming the metal comprises combining the precursor with a coreactant.

6. A method comprising:
   loading an integrated circuit device in a deposition chamber;
   depositing a transition metal precursor on the integrated circuit device; and
   decomposing the transition metal precursor with a coreactant;
   wherein the transition metal precursor is selected from the group consisting of:
   (i) a mononuclear cobalt monocarbonyl nitrosyl or cobalt dicarbonyl nitrosyl;
   (ii) a cobalt carbonyl bonded to one of a boron, indium, germanium and tin moiety;
   (iii) a mononuclear cobalt carbonyl bonded to a mononuclear or binuclear allyl; and
   (iv) a cobalt (II) complex comprising nitrogen-based supporting ligands selected from the group consisting of:

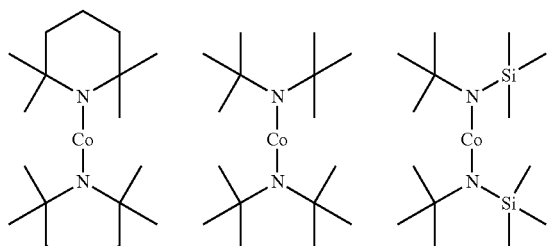

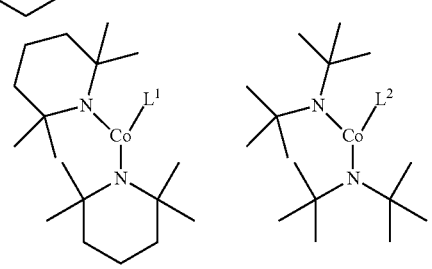

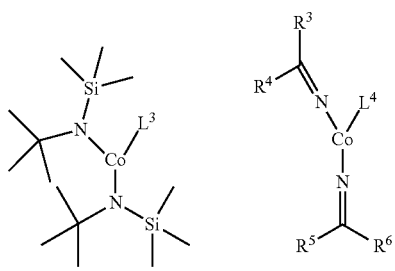

wherein $R^3$ is selected from a straight or branched monovalent hydrocarbon group have one to three carbon atoms and L is selected from $Me_2EtN$, $Me_3N$, $Et_3N$ and quinuclidine.

7. The method of claim 6, wherein the metal precursor comprises a mononuclear cobalt carbonyl nitrosyl selected from the group consisting of:

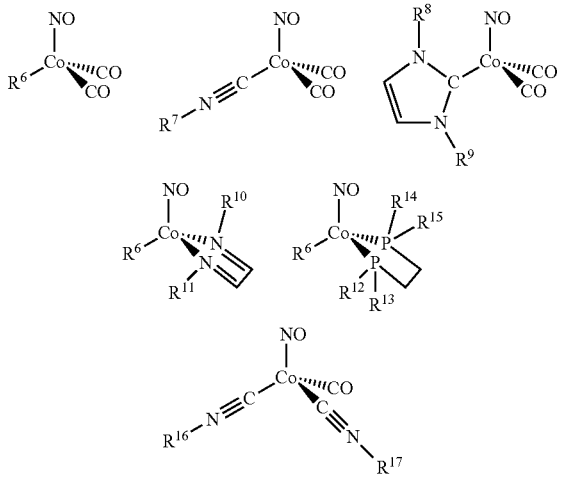

wherein $R^4$, $R^5$, $R^6$, $R^7$, $R^8$, $R^9$, $R^{10}$, $R^{11}$, $R^{12}$, $R^{13}$, $R^{14}$ and $R^{15}$ are independently selected from a straight or branched chain alkyl having one to the three carbon atoms.

8. The method of claim 6, wherein the metal precursor is selected from the group consisting of:

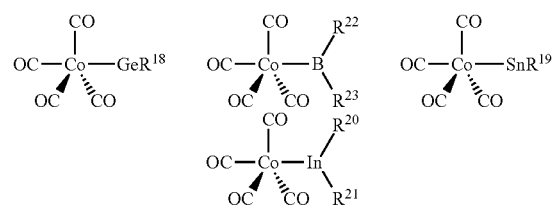

wherein $R^{22}$ and $R^{23}$ are independently selected from a straight or branched chain alkyl having one to the four carbon atoms and $R^{20}$ and $R^{21}$ may further individually be a substituted amine.

9. The method of claim 6, wherein the metal precursor is selected from the group consisting of:

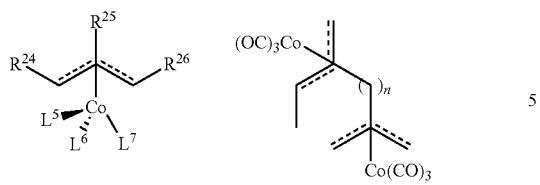

wherein $R^{24}$, $R^{25}$ and $R^{26}$ are independently selected from a straight or branched chain alkyl having one to the three carbon atoms and $L^2$, $L^3$ and $L^4$ are independently selected from the group consisting of:

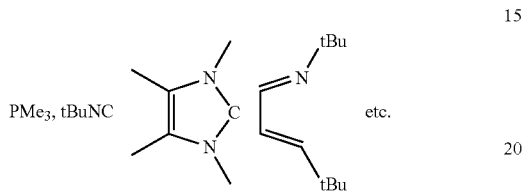

10. The method of claim 6, wherein the coreactant is selected from the group consisting of a hydrogen gas or plasma, an ammonia gas or plasma, a hydrazine, a borane, an alane and a silane.

* * * * *